US005663050A

United States Patent [19]

Bedell

[11] Patent Number: 5,663,050
[45] Date of Patent: *Sep. 2, 1997

[54] SENSOR FOR ANTIGEN-ANTIBODY REACTIONS

[75] Inventor: Glenn W. Bedell, Las Cruces, N. Mex.

[73] Assignee: Intelligent Monitoring Systems, Inc., Las Cruces, N. Mex.

[*] Notice: The term of this patent shall not extend beyond the expiration date of Pat. No. 5,543,329.

[21] Appl. No.: 240,847

[22] Filed: May 11, 1994

Related U.S. Application Data

[63] Continuation-in-part of Ser. No. 970,682, Nov. 3, 1992, Pat. No. 5,543,329.

[51] Int. Cl.[6] .................. G01N 33/536; G01N 33/558; G01N 33/574

[52] U.S. Cl. .................. 435/7.23; 356/306; 356/307; 356/318; 356/432; 356/433; 356/229; 422/82.05; 422/82.08; 422/82.09; 435/7.22; 435/808; 436/164; 436/172; 436/518; 436/531; 436/533; 436/534; 436/536; 436/538; 436/539; 436/541; 436/805; 436/807

[58] Field of Search .................. 356/307, 306, 356/318, 432, 433, 229; 422/82.05, 82.08, 82.09; 435/7.22, 7.23, 808; 436/518, 531, 533, 534, 536, 538, 539, 541, 164, 172, 805, 807, 810, 804

[56] References Cited

U.S. PATENT DOCUMENTS

| 3,492,396 | 1/1970 | Dalton et al. | 424/12 |
| 3,558,277 | 1/1971 | Laman et al. | 23/230 |
| 4,268,269 | 5/1981 | Proudfoot | 23/230 |
| 4,396,718 | 8/1983 | Proudfoot | 436/8 |
| 4,436,827 | 3/1984 | Tamagawa | 436/805 |
| 4,652,530 | 3/1987 | Rothman et al. | 436/92 |
| 4,908,676 | 3/1990 | Bedell et al. | 356/72 |

*Primary Examiner*—James C. Housel
*Assistant Examiner*—Christopher L. Chin
*Attorney, Agent, or Firm*—Deborah A. Peacock; Jeffrey D. Myers; Donovan F. Duggan

[57] ABSTRACT

A multi-purpose on-line or field-portable system and method for monitoring the presence and concentration of selected antigen-antibody reactions singly or in combination that result from the presence of specific microorganisms or free antigens present or suspended in aqueous solutions, during a given time period. The detection system comprises a detection column and two sensors mounted around the detection column. Each sensor consists of an electromagnetic radiation source and an appropriate detector for the electromagnetic radiation. The reacted analyte tends to accumulate at the sensor located at the bottom detection column. The lower sensor continually nulls against the upper sensor to subtract any optical effects due to non-reactants in the aqueous process or environmental stream. The response from the detector sensors drive an electric circuit, which provides an output signal. In the on-line automatic version, the signal can drive elements of a process system by switching automated valves.

36 Claims, 5 Drawing Sheets

SENSOR FOR ANTIGEN-ANTIBODY REACTIONS

CROSS-REFERENCE TO RELATED APPLICATIONS

This application is a continuation-in-part application of U.S. patent application Ser. No. 07/970,682, entitled "Detection of Selected Antigen-Antibody Reactions", to Bedell, filed on Nov. 3, 1992, now U.S. Pat. No. 5,543,329, the teachings of which are incorporated herein by reference.

BACKGROUND OF THE INVENTION

1. Field of the Invention (Technical Field)

This invention relates generally to the measurement of organisms and free antigens present or suspended in water by the detection of selected antigen-antibody reactions and more specifically to both a hand-held and on-line sensor for monitoring the concentration of organisms and free antigens.

2. Background Art

The detection of both organisms (i.e., bacteria, fungi, protozoans, algae, and viruses, both pathogenic and non-pathogenic) and selected organic pollutants in environmental fluid streams or in industrial process streams, including waste effluents, is becoming extremely important. Several prior art techniques exist for monitoring the concentration of organisms or selected organic pollutants in fluids, but each of these methods has several drawbacks in either environmental aqueous fluids or industrial process streams, including waste effluents in either a field or on-line industrial setting.

Standard microbiological procedures for detecting specific microbes and quantifying them includes several processes, all being time consuming and expensive.

One microbiological technique involves the drawing of a sample aliquot from the contaminated waters and the streaking of standard dilutions of that sample aliquot onto a selective agar growth medium which promotes the growth of the organism of interest. The streaked plates then are incubated under optimum growth conditions (temperature, pH, aeration, etc.) for the organism of interest for a period of time (usually 24 to 48 hours). The growth colonies appearing on the selective medium after the appropriate time period often must be examined under the microscope using staining techniques. This process often will yield related family or genera members, not a specific species or strain of a species. Often, the colonies of interest must be further subcultured one or more times on additional specific growth media in order to obtain definitive speciation or strain selection. Unless one is lucky with the first growth (i.e., showing countable, uniquely identifiable colonies), no quantification of species or strain can be made by this process, only the presence of family or genera members can be deduced.

Speciation or strain specificity techniques consist of mixing suspensions of specific colonies (obtained from the selective growth media, as described above) with specific polyclonal or monoclonal antibodies and observing the results of the formation of the antigen-antibody complex. Antigen-antibody agglutination complex formation reactions often can be seen by the naked eye. Fluorescent antigen-antibody complexes may be seen only by the use of a special fluorescent microscope. These tests, too, are usually qualitative. However, by making complicated standard dilutions and subsequent tests, lower threshold values for the different antigen-antibody complex formations may be determined for pure cultures. Newer techniques, using monoclonal-antibodies coated with colloidal gold, can provide specific and semi-quantitative estimations for selected microbes. At this time, even though the test specificity is very high, it is unknown whether these tests would be applicable to the rapid detection and enumeration of specific environmental water samples.

Detection of selected organic molecules using immunoassay techniques is relatively new. One new technique being used for selected organic molecules of interest is a haptenization technique. A hapten is a small molecule that is incapable of eliciting an antibody formation by itself, but can serve as a partial antigen if it is attached to the antigenic determinant of the larger, antigenic, macromolecule. The selected organic molecules of interest are haptenized onto the antigenic determinants of a selected macromolecule (antigan). An antibody is formed against the haptenized macromolecule by the injection of the haptenized molecule into a certain animal. A hapten-enzyme conjugate will mimic free organic molecules of interest and will compete for binding to the polyclonal antibody immobilized on a test tube. After washing to remove the unbound conjugate, a substrate chromogen is added and a colorized enzymatic reaction product is formed. The enzymatic reaction is stopped by the addition of a few drops of sulfuric acid, which changes the color to yellow. As with other competitive, enzyme-linked immunosorbent assays (ELISA), the color intensity of the enzymatic product is inversely proportional to the sample analyte concentration. Each sample must be run with a reference sample of deionized water. The optical density of the colored enzymatic product is read on a colorimeter or spectrophotometer. The ratio of the sample to the reference optical density values is used to estimate the selected organic chemical level, usually sensitive to the low parts per million (milligrams per liter) range. At this time, the technique seems to be restricted to estimating the level of polycyclic aromatic hydrocarbons in waters.

A more common method for determining the presence of selected organic molecules consists of collecting and measuring the molecules of interest by the use of one, or a combination of several, complicated techniques. These techniques include gas chromatography (GC), mass spectrometry (MS), high pressure liquid chromatography (HPLC), or combined techniques or instrumentation (e.g., GC-MS, HPLC-MS, etc.). In some cases, gas chromatography or liquid column chromatography used in conjunction with photometric detection has been used for organic substances which either absorb light or can be made to absorb light.

In each of the above methods of gas or liquid chromatography, the column uses a separation means for separating and individually detecting the molecules of interest. These column gas or liquid chromatography methods are not practical for either field or on-line sensors and the photometric measurements are subject to interference between different organic species contained in the sample which have similar retention times in the chromatographic column. Further, these methods require the injection of a sample and then waiting for the chromatographic column to separate the different species in time so that the concentration of each organic species in the sample can be determined by photometrically or electrically monitoring the effluent from the column. None of these methods would function adequately if a continuous stream sample were provided to the chromatographic columns.

In another method using chromatographic columns, Proudfoot, in U.S. Pat. No. 4,396,718 and U.S. Pat. No.

4,268,269, teaches a two step method for the detection of triazoles in an aqueous solution. A separation step removes the triazoles from the aqueous solution by adsorption onto a molecular resin. Next, an eluting solvent is passed through the molecular resin containing the previously adsorbed triazole. The eluting solvent desorbs the triazoles, and the eluate from the column is essentially free from impurities which would interfere with the quantification of the amount of triazole. In the quantification step, the eluate containing the triazole is passed through a column containing a cation exchange resin to which is bound a metal ion, wherein the triazole is strongly bound to the surface of the resin as a colored metal ion-triazole complex. After removal of uncomplexed metal from the column, the size and color of complexed metal-triazole bands formed on the column are visually compared with a known standard to determine the concentration of triazoles. This method is impractical for field or on-line monitoring because a visual measurement is necessary for quantification. Further, since the triazole is strongly bound to the surface of the resin as a colored metal iontriazole complex, the triazoles cannot be easily stripped from the column and the column reused for the next measurement.

Other methods use colorimetric techniques to detect organic molecules in an aqueous solution. For example, Rothman et al., U.S. Pat. No. 4,652,530, teaches a method for a colorimetric determination of isothiazolones in a fluid stream. The isothiazolones are first concentrated on a nonpolar adsorbent. The isothiazolones are stripped from the adsorbent and a reagent is used to break the aromatic ring of the isothiazolones. Then, another reagent is added to produce a colored complex. A conventional colorimetric analysis of the colored complex is used to determine the concentration of the isothiazolone.

Laman et al., U.S. Pat. No. 3,558,277, teaches a method for detecting biodegradable organics in aqueous solution in which the fluid stream is first mixed with a material to precipitate metals from the stream. The stream is filtered to remove the precipitate and then mixed with a permanganate solution and heated for 30–40 minutes. The solution is then diluted and colorimetrically analyzed.

Automated colorimetric methods rely on an expensive colorimeter to analyze the final product. The colorimetric equipment is not a compact self-contained unit that is easily installed in an on-line industrial setting.

Bedell, et al., U.S. Pat. No. 4,908,676, discloses an on-line analyte detection system (analyte detector) that detects both selected inorganic and organic analytes of interest which are dissolved in a process stream. A side stream is extracted through a motor-driven valve from the process stream, either by pressure relief or by pumping. The side stream flows through a detection column of an analyte detector and a sensor mounted around the detection column which detects the analyte by use of electromagnetic radiation and a sensor of that radiation. The side stream leaves the detection column and enters the line where the stream flows through a second motor-operated valve and then returns to the main process stream.

The sensor contains a source of electromagnetic radiation, typically a light source from a light emitting diode (LED), and an electromagnetic radiation detector, typically a Darlington phototransistor, and a detection that is transparent to the electromagnetic radiation source, typically a glass, plastic, or quartz tube. In one embodiment, the LED and the light detector are contained 180° apart in the sensor. Hence, the detector measures the light from the LED transmitted through the contents of the detection column. In another embodiment, the detector is located in the sensor so that the light from the LED is reflected by the contents of the detection column into the light detector. In yet another embodiment, the LED and the light detector are located at approximately 60° to 90° to each other such that the LED causes the contents of the detection column to fluoresce and the light detector (shielded from the incident light by the appropriate cut-off or interference filter) measures the fluorescent light.

Accordingly, the optical properties of the analyte and/or the adsorbed analyte define the configuration of the sensor that is used in the inline detector. If the analyte in the process stream has electromagnetic radiation absorption, scattering, transmission, or emission properties that can be detected by the sensor, the side stream is simply passed through the detection column and the electromagnetic radiation properties are detected by the sensor.

If the analyte does not have the necessary optical properties, or if it is desired to measure the total amount of analyte in the process stream in a given period, the detection is packed with an adsorbent so that as the side stream from the main line flows through the detection column, the adsorption of the analyte species of interest in the side stream flow forms a complex on the adsorbent, removes the analyte from the side stream and effectively concentrates the analyte so that its presence is easily detected by the sensor. Also, the complex formed on the adsorbent may have a significantly different extinction coefficient from the analyte itself. Accordingly, the formation of the complex on the adsorbent enhances the capability of detecting the presence of the analyte in the process stream.

A controller is used to sequence the operation of the on-line analyte detector. Initially, the controller holds closed the motor-operated valve to a first reagent tank, the motor-operated valve to a second reagent tank containing an eluent, and the motor-operated valve to the waste recovery system. The controller activates a timer, which determines the sampling period, i.e., the prescribed time interval, of the analyte detector, and opens the valves so that the side stream starts to flow though the on-line analyte detector. While motor-operated valves are used in this embodiment, any valve, which can be remotely controlled, can be used in the system.

In response to the detector sensor function, the sensor circuit energizes the alarm to alert personnel of the process stream concentration or deviations from some predetermined value and energizes a circuit in the controller which takes the analyte detector off-line prior to the end of the sampling period, etc. The controller then aligns the eluent reagent tank with the detection column for stripping.

Some analytes do not have an absorption or emission spectrum which is detectable, and other analytes are not conveniently adsorbed on any matrix even though the analyte has acceptable electromagnetic spectral characteristics. In these cases, the analyte detector utilizes either a reaction product of the analyte wherein the reaction product has acceptable optical properties, or the reaction product is better adsorbed on the adsorbent in the detection column. In these instances, the controller is set so that a motor-operated valve to one of the reagent tanks and the reagent in the reagent tank is metered into the side stream in line before entry into the detector column. The interaction of the reagent with the analyte in the side stream produces a product which has detectable spectral properties and/or which is adsorbed on the adsorbent in the detection column. The sensor is set as previously described, and the operation of the analyte detector also is as previously described.

The analyte detectors are placed in an opaque container to prevent external electromagnetic radiation from affecting the readings of the photodetector contained within the sensor. The patent of Bedell et al., also describes an embodiment in which both the electromagnetic source and the sensor are mounted outside of the body of the sensor. In this embodiment, a first fiber optic cable is secured at the position of the incident source, typically the LED, and the second fiber optic is secured at the position of the sensor, typically the phototransistor position on the analyte detector collar. The cables are secured in the holes so that they are flush with the inner surface of the sensor body formed by the hole for the detection column. One of the fiber optic cables is connected to a light source (LED, laser, etc.) outside the sensor body and the other fiber optic cable is connected to the photodetector which also now is outside the sensor body. This embodiment permits the use of larger, and in certain cases, more sensitive, light sources and photodetectors.

Each of the prior art systems suffers from several deficiencies which make the field and on-line detection of microorganisms and selected organic molecules in aqueous solution impractical, particularly from the points of specificity, time, and expense. Microbiological techniques are especially time consuming and expensive, with specific immunoassay procedures generally being followed as adjuncts to the original isolation techniques. Also, the latter techniques which may have field applications generally require the presence of large numbers of the organism of interest. Current immunoassay techniques are not being used as on-line sensors. Liquid or gas chromatographic and mass spectrographic equipment are both complex and expensive. The chromatographic methods primarily are designed to distinguish multiple ions (organic chemical) and the concentration of each ion (organic chemical). Chromatographic methods generally are not suitable for either continuous monitoring or the monitoring of the amount of ion or organic chemical in a mixed process stream during a specific time period. The process of Bedell et al., does provide an exception for allowing the on-line determination of selected organic molecules, but it does not allow for the detection of microorganisms or the use of immunoassay techniques for determining selected organic analytes.

SUMMARY OF THE INVENTION

Disclosure of the Invention

In accordance with the present invention there is provided an apparatus for the detection of selected antigen-antibody reactions in undissolved substances and fluids.

The preferred sensor for detecting selected antigen-antibody reactions comprises a tube shaped reaction chamber for mixing a preselected amount of a pH adjusted aqueous solution to be tested with an antibody, a heater for increasing a speed of an antigen-antibody reaction of the pH adjusted aqueous solution and the antibody, a first sensor affixed to the tube shaped reaction chamber for detection of an analyte and interference from the antigen-antibody reaction, a second sensor affixed to the tube shaped reaction chamber at a predetermined distance from the first sensor for detection of the analyte relative to the interference, structure for nulling a second sensor output to the first sensor output to negate the interference, and a differential signal from the first and second sensor representative of a presence of a predetermined concentration of the analyte.

The preferred heater heats the reaction chamber. The preferred heater heats the reaction chamber to a temperature between 40 to 50 degrees Fahrenheit.

The first and second sensors are preferably affixed to a housing and the tube shaped reaction chamber is set in an aperture in the housing. The first and second sensors each preferably comprise a light emitting source and a light detector for detecting scattering and absorption. The preferred light detectors comprise photo transistors. The first and second sensors each can further comprise an ultraviolet light source and a fluorescence detector.

The preferred structure for nulling comprises continually nulling said second sensor output from said first sensor output.

The preferred method of detecting selected antigen-antibody reactions comprises the steps of adjusting the pH of the aqueous solution to be tested, heating and cooling the pH adjusted solution to be tested for precipitation of inorganics in the solution, filtering out the precipitated inorganics from the solution, providing a preselected antibody to the solution, heating the antibody and solution, cooling the antibody and solution to ambient temperature to reduce a convection current, shaking the cooled antibody and solution, nulling a second sensor output from a first sensor output, and providing a differential signal from the first and second sensor outputs representing a presence of a selected analyte.

One object of the present invention is a detection system for antibody-antigen reaction that detects more rapidly than presently available systems.

Another object and advantage of the present invention is the ability to detect lower levels of antibody-antigen complex formations compared to presently available systems.

Yet another advantage is the ability to observe and detect large molecules that can be "tagged" with fluorescent or luminescent probes.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

DESCRIPTION OF THE PREFERRED EMBODIMENTS

Best Modes for Carrying Out the Invention

The present invention is an apparatus and method for simple, multipurpose, field and on-line systems for monitoring the presence, the concentration and/or the total amount of microorganisms or selected organic analyte species in an aqueous solution by the detection of antigen-antibody reactions. The apparatus is compact, self-contained, and functions in any setting where it is necessary to monitor the presence of either selected microorganisms or organic chemicals using selected immunoassay (antigen-antibody) reactions.

This invention has two physical configurations, one for hand-held field applications, and another for use as an on-line sensor. The apparatus and method detect the presence of a predetermined threshold of whole microorganisms using selected antigen-antibody reactions. These microorganisms include bacteria, algae, fungi, protozoans, and viruses. The presence of certain threshold biological products can be detected for which antibodies have been or can be made.

The apparatus and method can be used to detect a presence of selected organic molecules for which antibodies have been or can be made, including by the result of their being haptenized.

The preferred embodiment comprises means for calibrating a predetermined calibratian for the quantitation of the detected analytes, and means for indicating quantities above a preset threshold value of interest. The preferred field apparatus is operable from any 12 volt DC source such as battery, automobile cigarette lighter, solar panel, AC-DC converter.

The preferred system has dual beam sensors that constantly null against an upper, in-line sensor of a detector. This provides for greater signal sensitivity and stability, but it permits the subtraction of any interference due to non-reacted antibody, microbes other than analyte of interest, or due to non-antibody reactive debris present in sample or the stream being analyzed. An alternate embodiment can be used for a measurement of radioactively labeled analyte or antibody.

The preferred embodiment also has a sensitive dual beam detector for transmission and fluorescence change detection. Alternative designs can be used for detection of radioactively-labeled antigen-antibody reactions. The preferred system has column heaters which can speed the rates of reactions for selected immunoassay techniques, particularly agglutination and co-agglutination reactions for either polyclonal or monoclonal antibody-antigen complex formation and presence. The preferred apparatus and method comprise means for determining an antigen-antibody reaction for predetermined antibodies that have been labeled with fluorescent or radioactive "tags", or with chromogens or chromophores. Additionally, the preferred method and system comprise detecting mixed antigen-antibody reactions. The means and method of detecting comprise a fluorescent monoclonal antibody designed to bind to one region of a microbe added together with a monoclonal or polyclonal agglutination or co-agglutination antibody that has been designed to bind to a different region of the same microbe in microbiological determinations. A specific increase in fluorescence together with agglutination clumping reduces reactions due to any non-specific binding that might create a false positive signal.

Again, the invention can be configured as an on-line or hand held sensor. Although this description below is directed to detection of cholera, the invention can be utilized for detection of several different organisms and free antigens.

Figure 1:
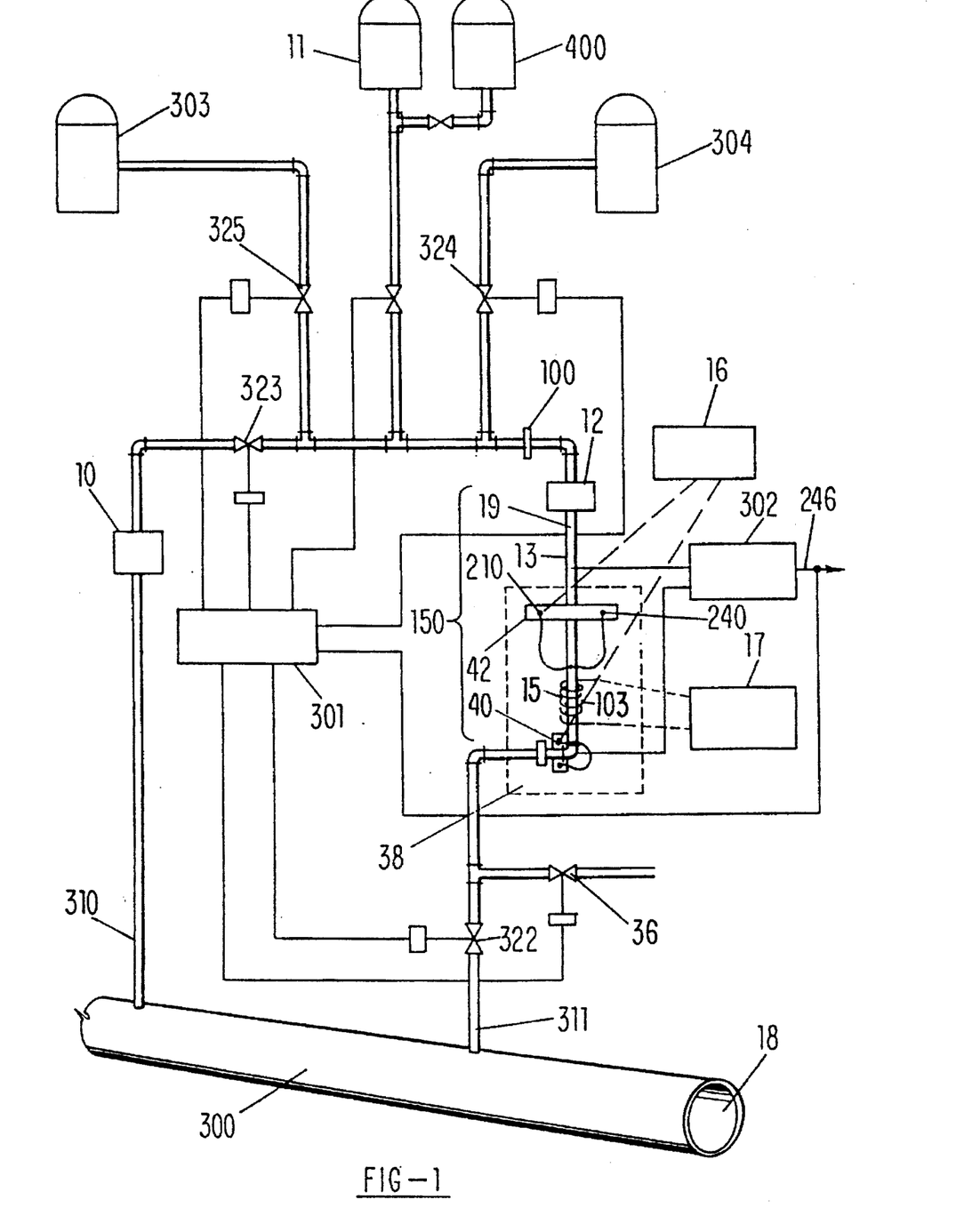
FIG. 1 is a diagram of the preferred on-line stream apparatus and method.

FIG. 1 illustrates the preferred embodiment of the invention. Aqueous analyte-containing solution 18 is drawn from primary process stream 300 or environmental waters by endogenous pressure or by pumping (not shown). Aqueous analyte-containing solution 18 goes through settling basin and filter 10 where it is filtered through a five micron filter or the like to remove debris. Filtered aqueous analyte 18 proceeds and is metered into mixing chamber 12 where it is pH-adjusted by addition of buffer 303 and rapidly mixed with the proper amount of antibody 11. If appropriate, a second antibody 304 is provided. The preferred mixing chamber 12 is a coil of glass tubing that is contiguous with a sensored column region. The preferred glass tubing is heavy-walled with a 1.0 cm outside diameter or the like. Mixing chamber reactants 303, 11 and 304 are discharged into reaction chamber 13 or sensor column region 103 so that analyte-antibody reactant mixture 18, 303, 11 and 304 (hereinafter reaction mixture 19) is located and covers the center of both sensors 42 and 40. High intensity fluorescent light source 16 illuminates this area. Chamber 13 is slightly J-shaped so that reactants will accumulate at the lower detector sensor 40.

Heater 15 is then turned on. The preferred heater 15 is a pulse-type heater that maintains but does not exceed an upper temperature limit for the reaction temperature. The temperature of heater 15 is controlled by an interface with a thermistor on heater 15 and heater circuit 17. During the reaction step a signal is obtained from sensor 42 and constantly compared with the signal obtained from sensor 40. This process improves the sensitivity by electronically subtracting in sensor circuit 302, anything in analyte solution 18 or reaction mixture 19 other than the analyte that is reacting with the antibody. This would include unreacted reactants such as unbound antibody and/or analytes, including microbes different from the one specifically reacting with the antibody, dirt, and debris.

An operator can calibrate the signal to prepare a quantitative table that correlates with the signal above a minimum threshold of detection. After the sensor circuit 302 has made its signal decision yes or no, the analyte sample 18 or reaction mixture 19 is discharged by opening waste recovery valve 36. Once analyte 18 or reaction mixture 19 has been drained, the system is flushed with two or more rinses of distilled water 400, or the like, through reaction chamber entry 100.

Figure 8:
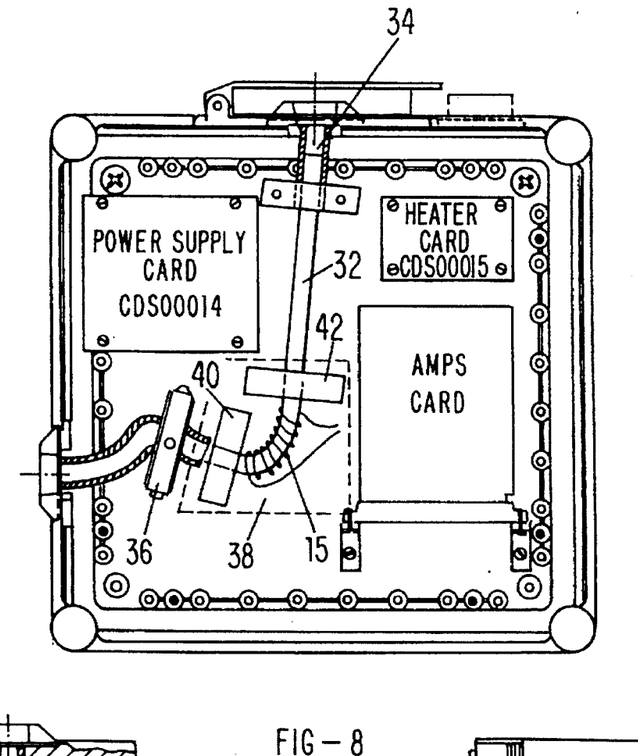
FIG. 8 is a front view of the preferred hand-held field detector.
Figure 9:
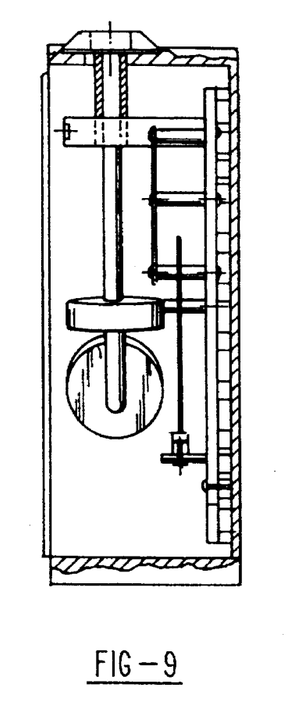
FIG. 9 is a cut out side view of the detector of FIG. 8.
Figure 10:
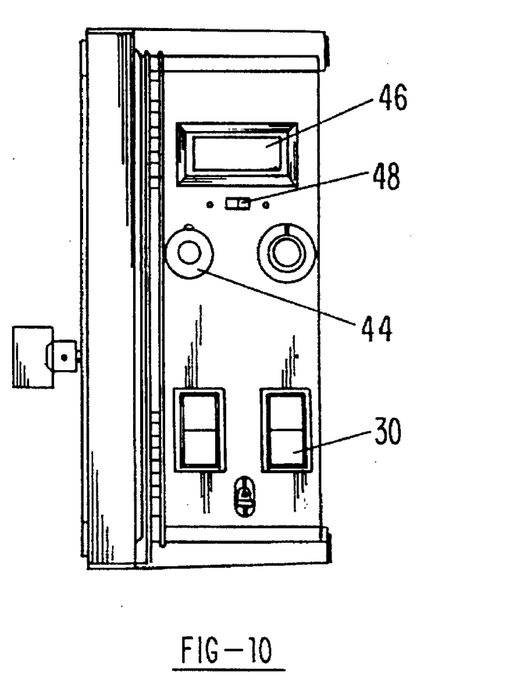
FIG. 10 is a side view of the detector of FIG. 8.

A field detection unit is illustrated in FIGS. 8, 9 and 10. The field unit can be battery powered and activated by switch 30. In utilizing the field unit, the drawing of a sample, pH adjustment, filteration, and mixing of the antibody with the analyte are done by hand (not shown). Analyte-antibody reaction mixture is added by pipette or by syringe (not shown), to reaction chamber 32 through port 34, after drain valve 36 has been closed. In one embodiment, the preferred amount added is approximately 3 ml of analyte and 100 microliters of antibody. The reaction chamber is slightly J-shaped 38 so that reactants will accumulate at the lower detector sensor 40. Heater 15 is then turned on if desired or necessary. The heating step may be omitted depending on the reaction type. Sensor signals from 42 and 40 are nulled to a predetermined value by turning transmittance knob 44 and observing the values on meter 46. Signal changes are recorded preferable every two to five minutes for a total lapse time of 15 to 30 minutes depending on the reaction type and the predetermined speed of agglutination and co-agglutination reaction with or without heating.

As an example, in order to detect cholera the sample is mixed with a co-agglutination antibody such as "cholera reagent" from New Horizon's Diagnostics. The mixture is added by pipette or syringe through port 34 to reaction chamber 32. Heater 15 is turned on to speed up the binding of the antibody that has been bound onto killed staphylococcal cells. The co-agglutination antibody is monoclonal and binds to the region of the cholera cell. Sensor signals 42 and 40 are nulled to a predetermined value. Once the binding occurs the reactants accumulate towards lower detector sensor 40. Signal changes are recorded for a predetermined lapse time and compared to a buffer plus antibody (no analyte). If the signals differ by a predetermined amount the test is deemed positive for cholera.

Figure 2:
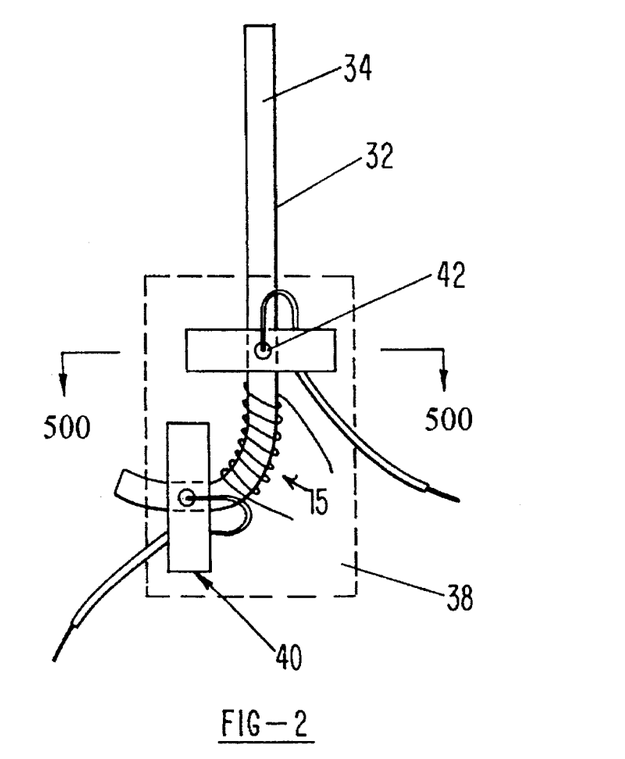
FIG. 2 is a front view of the preferred sensor.
Figure 3:
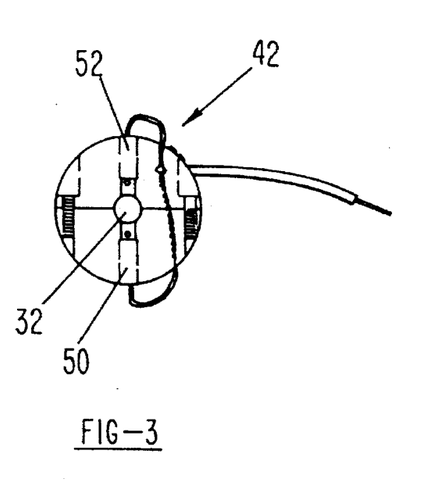
FIG. 3 is a top view of the preferred sensor of FIG. 2.
Figure 4:
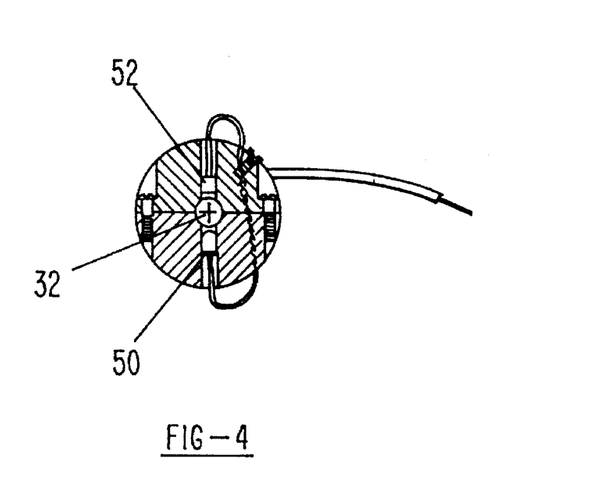
FIG. 4 is cut out view of the sensor of FIG. 2.

FIG. 2 shows the preferred reaction chamber 22 with the preferred sensor 40 and 42 locations. Also shown is the preferred heater 15. FIG. 3 is a top view of the preferred sensor 42. Sensor 40 is similar. Light Emitting Diode (LED) 50, or the like, is placed on one side or reaction chamber 32 and photo transistor 52, or the like, is placed directly on the opposite side of reaction chamber 32. FIG. 4 is a cut away view of FIG. 3.

The relative values obtained are compared to values obtained for buffer plus antibody (no analyte) and buffered analyte plus antibody. If the signals differ by a predetermined amount, the test is determined to be positive, signifying the analyte is present above a certain minimum threshold. The minimum threshold value is determined empirically by using known standards. After the proper test time interval, drain valve 36 is opened and the system is drained and flushed two or more times with distilled water (not shown) or the like. After draining and flushing, drain valve 36 is closed and the system is ready.

Figure 5:
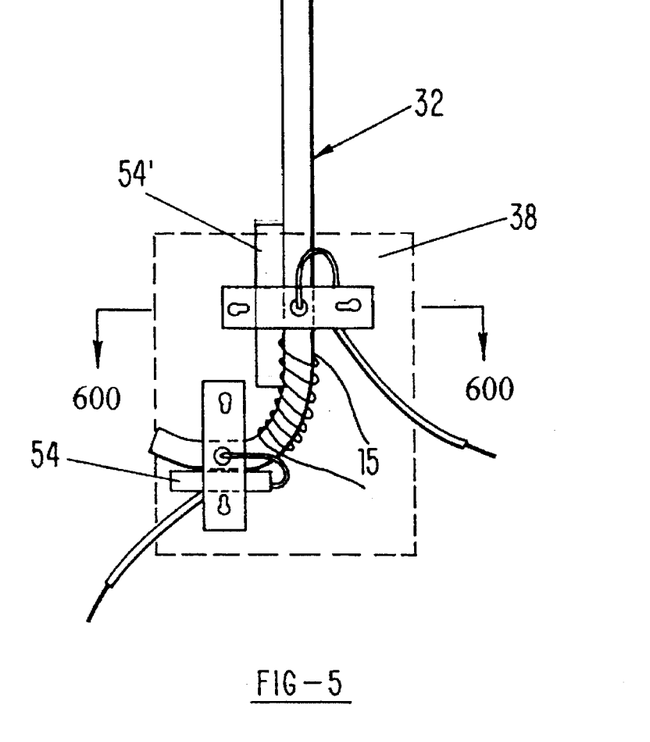
FIG. 5 is a front view of an alternative sensor.
Figure 6:
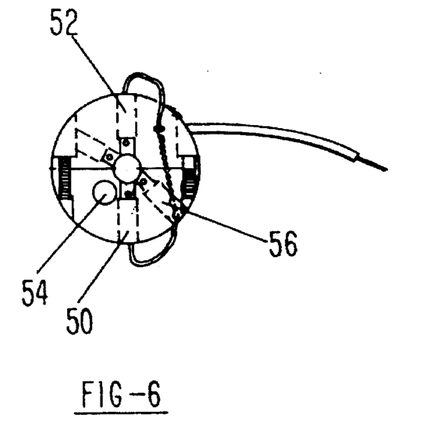
FIG. 6 is a top view of the sensor of FIG. 5.
Figure 7:
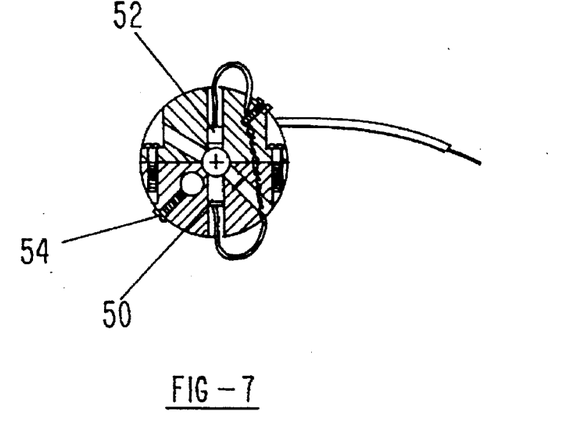
FIG. 7 is a cut out view of the sensor of FIG. 5.

When using a fluorescently "tagged" antibody, the antibody is mixed with an agglutination or co-agglutination antibody, and both added to the analyte aliquot during the mixing step. This is illustrated in FIGS. 5, 6 and 7. After the addition of the reaction mixture to the sensor column, initially both the transmittance and the fluorescence of the reaction mixture is nulled. Selection of the mode to be determined, transmittance versus fluorescence, is done via mode switch 48. FIG. 5 is a side view of the alternative embodiment for detection of fluorescence. The apparatus is similar to the preferred embodiment except that ultraviolet (UV) tubes 54 and 54', or the like, are positioned next to reaction chamber 32 as shown. FIG. 6 is a top view of the alternative embodiment showing second photo transistor 56. After agglutination has taken place, the fluorescence mode is selected and the fluorescence signal determined. A predetermined level of transmittance and fluorescence signal combined would verify the presence of the analyte of interest, particularly if monoclonal antibodies are used as at least one of the antibodies.

The present invention can detect antigenic determinants on whole cells that are in waters or molecules which are or can become antigenic (haptens) and will permit rapid and specific detection of these cells or molecules from waters or process streams. In one embodiment, bacterial disease organisms can rapidly and continuously be detected from various water sources. Additionally, this invention can be used to detect other waterborne disease organisms such as, but not limited to, schistosomiasis, leishmaniasis and salmonellosis. Also, viral organisms and toxic molecules in food or cosmetic process lines, for example, aflatoxin in peanut butter, can be detected. Haptenic molecules such as benzene, toluene and xylene can be induced to form antibodies which can be detected using this invention.

Figure 11:
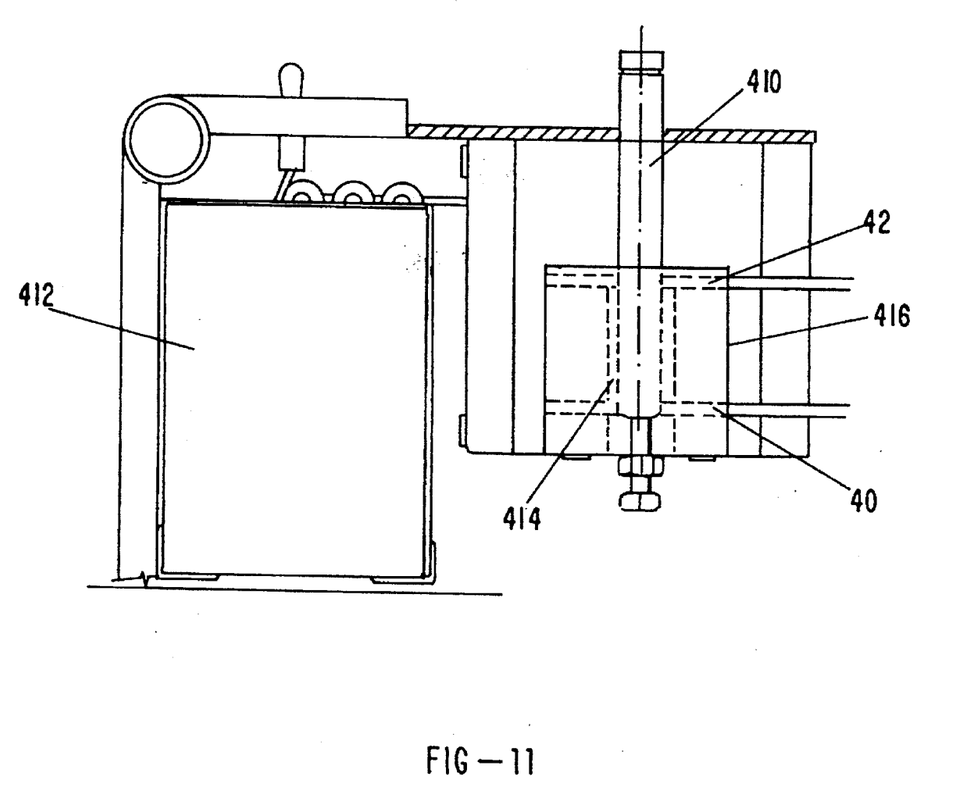
FIG. 11 depicts another embodiment of the reaction chamber and heater.

FIG. 11 depicts the preferred embodiment of reaction chamber 410 and heater 412. Reaction chamber 410 is a straight tube shaped member. Reaction chamber 410 is preferably constructed of a glass tube or cuvette with an outside diameter of approximately 1.0 mm. Although the preferred embodiment has been described utilizing specific materials and configurations, reaction chamber 410 can be of other materials, different configurations and different dimensions, for example, an enclosed vessel such as an ordinary test tube. As shown in FIG. 11, reaction chamber 410 is set in an aperture 414 in sensor block 416. Sensors 42 and 40 are each affixed to sensor block 416. Sensors 42 and 40 can comprise the embodiment for detecting scattering and absorption, FIGS. 3 and 4, or for measuring fluorescence, FIGS. 6 and 7.

The preferred heater 412 is also shown in FIG. 11. Heater 412, is positioned adjacent to reaction chamber 410. The preferred heater is a pulsed type heater that automatically shuts off after a prescribed period of time. The heater 412 operates during the reaction period of the process to increase the speed of the reaction within reaction chamber 410. The optimal range for increasing the speed of reaction is between 40 and 50 degrees F. The heater also preferably turns off automatically after approximately 5 minutes of operation. Although this embodiment describes a specific type heater and its configuration in relation to the reaction chamber 410, this disclosure is intended to include any heating apparatus for heating reaction chamber 410.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application are hereby incorporated by reference.

What is claimed is:

1. Apparatus for detecting an analyte by using selected antigen-antibody reactions comprising:

tube shaped reaction chamber means for mixing a preselected amount of a pH adjusted aqueous solution to be tested with an antibody;

heater means for increasing a speed of an antigen-antibody reaction of said pH adjusted aqueous solution and said antibody;

a first sensor means affixed to said tube shaped reaction chamber means for detection of an analyte and interference from said antigen-antibody reaction, said first sensor means producing a first sensor output;

a second sensor means affixed to said tube shaped reaction chamber means at a predetermined distance from said first sensor means for detection of the analyte relative to the interference, said second sensor means producing a second sensor output;

means for nulling said second sensor output from said first sensor output to negate the interference; and means for producing a differential signal representative of a presence of said analyte.

2. The apparatus of claim 1 wherein said heater means comprises means for heating said reaction chamber.

3. The apparatus of claim 2 wherein said means for heating said reaction chamber comprises means for heating said reaction chamber between 40 to 50 degrees Fahrenheit.

4. The apparatus of claim 1 wherein said first and second sensors are affixed to a housing and said tube shaped reaction chamber is set in an aperture in said housing.

5. The apparatus of claim 4 wherein said first and second sensors each comprise a light emitting source and a light detecting means for detecting scattering and absorption.

6. The apparatus of claim 5 wherein said light detecting means comprise photo transistors.

7. The apparatus of claim 5 wherein said light emitting source comprises an ultraviolet light source and said light detecting means comprises a fluorescence detection means.

8. The apparatus of claim 1 wherein said means for nulling comprises continually nulling said second sensor output from said first sensor output.

9. A method of detecting an analyte by using selected antigen-antibody reactions, the method comprising the steps of:

a) adjusting the pH of an aqueous solution to be tested;

b) filtering out precipitated inorganics from the solution;

c) providing a preselected antibody specific for the analyte to the solution;

d) heating the antibody containing solution;

e) cooling the antibody containing solution to ambient temperature to reduce a convection current;

f) shaking the cooled antibody containing solution;

g) nulling a second sensor output from a first sensor output, wherein said first and second sensor outputs are acquired subsequent to step f); and h) providing a differential signal from the first and second sensor outputs representing a presence of a selected analyte.

10. A method of detecting an analyte in a solution by using selected antigen-antibody reaction, the method comprising the steps of:

a) providing said solution in a reaction chamber for containing an antigen-antibody reaction;

b) providing a preselected antibody to said reaction chamber;

c) outputting a first signal from a first sensor proximate the reaction chamber;

d) outputting a second signal from a second sensor proximate the reaction chamber; and e) nulling the second signal from the first signal, and thereby outputting a third signal indicative of an antigen-antibody reaction for detection of said analyte.

11. The method of claim 10 wherein the step of providing a reaction chamber comprises providing a J-shaped reaction chamber.

12. The method of claim 10 wherein the step of providing a reaction chamber comprises providing a straight glass tube reaction chamber.

13. The method of claim 10 wherein the step of providing a reaction chamber comprises providing an enclosed vessel reaction chamber.

14. The method of claim 10 wherein the analyte to be detected comprises a member selected from the group consisting of antigens and antibodies.

15. The method of claim 10 wherein the analyte to be detected comprises a cholera analyte.

16. The method of claim 10 wherein the analyte to be detected comprises a member selected from the group consisting of haptens and macromolecules.

17. The method of claim 10 further comprising the step of heating the reaction chamber.

18. The method of claim 10 wherein the antigen-antibody reaction is an agglutination reaction.

19. The method of claim 10 wherein the antigen-antibody reaction is a co-agglutination reaction.

20. The method of claim 10 wherein the step of nulling the second signal from the first signal comprises nulling a first transmittance signal and a second electromagnetic radiation transmittance signal.

21. The method of claim 10 wherein the step of nulling the second signal from the first signal comprises nulling a first fluorescent signal and a second fluorescent signal.

22. The method of claim 10 wherein the step of nulling the second signal from the first signal comprises nulling a first light transmittance signal and a second fluorescent signal.

23. The method of claim 10 wherein the step of nulling the second signal from the first signal comprises nulling a first fluorescent signal and a second light transmittance signal.

24. The method of claim 10 wherein the step of nulling a second signal from a first signal comprises nulling a first radioactive signal and a second radioactive signal.

25. An apparatus for detecting an analyte comprising:

a reaction chamber;

a first sensor proximate said reaction chamber for outputting a first signal;

a second sensor proximate said reaction chamber for outputting a second signal; and means for nulling said second signal from said first signal, and thereby outputting a third signal indicative of the analyte to be detected.

26. The apparatus of claim 25 wherein said reaction chamber comprises a J-shape.

27. The apparatus of claim 25 wherein said reaction chamber comprises a straight tube.

28. The apparatus of claim 25 wherein said reaction chamber comprises an enclosed vessel.

29. The apparatus of claim 25 further comprising a heater.

30. The apparatus of claim 25 wherein said means for nulling said second signal from said first signal comprises means for nulling a first transmittance signal and a second electromagnetic radiation transmittance signal.

31. The apparatus of claim 25 wherein said means for nulling said second signal from said first signal comprises means for nulling a first fluorescent signal and a second fluorescent signal.

32. The apparatus of claim 25 wherein said means for nulling said second signal from said first signal comprises means for nulling a first fluorescent signal and a second light transmittance signal.

33. The apparatus of claim 25 wherein said means for nulling said second signal from said first signal comprises means for nulling a first light transmittance signal and a second fluorescent signal.

34. The apparatus of claim 25 wherein said analyte to be detected comprises a member selected from the group consisting of antigens and antibodies.

35. The apparatus of claim 25 wherein said analyte to be detected comprises a cholera analyte.

36. The apparatus of claim 25 wherein said analyte to be detected comprises a member selected from the group consisting of haptens and macromolecules.

* * * * *